(12) United States Patent
Webler et al.

(10) Patent No.: US 8,197,441 B2
(45) Date of Patent: Jun. 12, 2012

(54) CATHETER MOUNTED AUTOMATIC VESSEL OCCLUSION AND FLUID DISPERSION DEVICES

(75) Inventors: William E. Webler, Escondido, CA (US); Gary Hague, Carlsbad, CA (US); Frank E. Manning, Temecula, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 369 days.

(21) Appl. No.: 11/295,419

(22) Filed: Dec. 6, 2005

(65) Prior Publication Data
US 2007/0129752 A1    Jun. 7, 2007

(51) Int. Cl.
*A61M 31/00*    (2006.01)
(52) U.S. Cl. ............... 604/103.01; 604/103.09; 604/104
(58) Field of Classification Search ............... 604/96.01, 604/97.01, 99.01, 99.04, 103, 103.01, 104, 604/256, 509, 907, 915, 920, 99.02, 99.03, 604/101.02, 103.03, 103.12, 103.13, 103.14, 604/105, 106, 103.06, 103.09, 103.11; 600/192, 600/193, 194, 196, 200; 606/192, 193, 194, 606/196, 200
See application file for complete search history.

(56) References Cited

U.S. PATENT DOCUMENTS

| | | | | |
|---|---|---|---|---|
| 3,742,960 A | * | 7/1973 | Dye et al. | 604/99.03 |
| 3,901,272 A | * | 8/1975 | Banners et al. | 137/513.5 |
| 4,813,934 A | * | 3/1989 | Engelson et al. | 604/99.02 |
| 4,921,478 A | * | 5/1990 | Solano et al. | 604/509 |
| 4,998,539 A | * | 3/1991 | Delsanti | 128/898 |
| 5,098,418 A | * | 3/1992 | Maitz et al. | 604/319 |
| 5,306,250 A | * | 4/1994 | March et al. | 604/104 |
| 5,454,789 A | * | 10/1995 | Burns et al. | 604/99.04 |
| 5,533,987 A | * | 7/1996 | Pray et al. | 604/527 |
| 5,628,730 A | * | 5/1997 | Shapland et al. | 604/21 |
| 5,843,069 A | * | 12/1998 | Butler et al. | 604/891.1 |
| 5,868,776 A | * | 2/1999 | Wright | 606/194 |
| 6,312,407 B1 | | 11/2001 | Zadno-Azizi et al. | |

(Continued)

FOREIGN PATENT DOCUMENTS
EP    0 330 376 A2    8/1989
(Continued)

OTHER PUBLICATIONS

"Hug". Merriam-Webster Online Dictionary. <http://www.merriam-webster.com/dictionary/hug>.*

(Continued)

*Primary Examiner* — Kevin C Sirmons
*Assistant Examiner* — Kami A Bosworth
(74) *Attorney, Agent, or Firm* — Blakely, Sokoloff, Taylor & Zafman LLP (57) ABSTRACT

Catheter or guidewire mounted automatic vessel occlusion and fluid dispersion devices that expand to occlude or partially occlude a vessel when a fluid is flowing in the catheter or guidewire, and that automatically collapse when fluid flow is stopped. Each occlusion device has an elastic skeleton covered with a flexible cover coupled thereto and may have a hole(s) or openings in its distal or proximal end thereof to allow controlled flow through the desired end of the occlusion device. The fluid may be a flush fluid for enabling or improving the performance of imaging devices and image enhancing fluids, of treatment fluids for localized treatment of a vessel or tissues in communication with the vessel and/or of the transmission of energy to the vessel wall and adjacent tissues. Various embodiments are disclosed.

20 Claims, 10 Drawing Sheets

U.S. PATENT DOCUMENTS

| | | | |
|---|---|---|---|
| 6,458,096 B1 * | 10/2002 | Briscoe et al. | 604/96.01 |
| 6,485,500 B1 * | 11/2002 | Kokish et al. | 606/194 |
| 6,540,722 B1 * | 4/2003 | Boyle et al. | 604/106 |
| 6,695,811 B2 * | 2/2004 | Samson et al. | 604/103.01 |
| 2002/0165521 A1 * | 11/2002 | Cioanta et al. | 604/509 |
| 2003/0120303 A1 | 6/2003 | Boyle et al. | |
| 2003/0144685 A1 | 7/2003 | Boyle et al. | |
| 2003/0195505 A1 | 10/2003 | Hassett et al. | |
| 2003/0212361 A1 | 11/2003 | Boyle et al. | |
| 2003/0236443 A1 * | 12/2003 | Cespedes et al. | 600/29 |
| 2004/0006361 A1 | 1/2004 | Boyle et al. | |
| 2004/0055606 A1 * | 3/2004 | Hendricksen et al. | 128/207.14 |
| 2004/0098032 A1 | 5/2004 | Papp et al. | |
| 2004/0162575 A1 * | 8/2004 | Wu et al. | 606/194 |
| 2005/0137681 A1 * | 6/2005 | Shoemaker et al. | 623/1.23 |
| 2005/0288632 A1 * | 12/2005 | Willard | 604/103.01 |
| 2006/0009748 A1 * | 1/2006 | Mathis | 604/509 |
| 2006/0052814 A1 * | 3/2006 | Sater | 606/200 |

FOREIGN PATENT DOCUMENTS

| | | |
|---|---|---|
| EP | 0 567 788 A1 | 11/1993 |
| WO | WO 02/22046 A2 | 3/2002 |

OTHER PUBLICATIONS

PCT Search Report and Written Opinion for PCT/US2006/045166, mailed Oct. 24, 2007, 16 pages.

Advanced Polymers Incorporated, Product Information for Mocroporous/Drug Delivery Balloons, 2001.

* cited by examiner

CATHETER MOUNTED AUTOMATIC VESSEL OCCLUSION AND FLUID DISPERSION DEVICES

BACKGROUND OF THE INVENTION

1. Field of the Invention

The present invention relates to the field of occlusion/infusion and occlusion/imaging devices and systems.

2. Prior Art

It is increasingly important that a physician or surgeon delivering substances, such as a treatment agent or drug or an image-enhancing agent, is able to efficiently and accurately locate and/or effectively deliver the substance to the desired target tissue. This is particularly true when the concentration of the substance required at the target site cannot be safely or effectively achieved by introduction of the substance to a location remote from the target site or the flow of blood washes away or dilutes the substance too rapidly at the target site. Moreover, the physician may only want to treat the diseased portion of a vessel, organ or tissue and avoid treating the healthy portions.

For example, to achieve localized treatment of tissue, such as tissue in a heart, physicians and surgeons can use catheters and/or guidewires, which may include a balloon(s) and an inflation lumen(s) for use as an occlusive device. Specifically, cardiovascular guide catheters are generally percutaneous devices used to advance through a vasculature of a patient to a region of interest and are devices through which another catheter or device may be inserted. Also, guide catheters commonly have imaging agents injected through their lumen to aid in their positioning and to aid in the visualization of a vascular region of interest. Guide catheters are generally inserted into a proximal percutaneous vascular access site via the inner diameter of a shorter catheter-like device, an introducer. Delivery catheters are generally catheters used to deliver a treatment agent(s) and/or diagnostic device(s) to a region of interest in a vasculature of a patient and typically may be inserted through another catheter (e.g., a guide catheter) while engaged with a guidewire. Delivery catheters may be provided with a lumen(s) and a port(s) to allow the delivery of fluids into the vasculature at the distal end of the delivery catheter and/or at a port(s) along the length of the catheter. Guidewires are generally devices that engage a guide catheter or delivery catheter and are used to guide them through a vasculature of a patient to a region of interest and are typically inserted into the vasculature through another catheter (e.g., the guide catheter, the delivery catheter) or while engaged with another catheter. Typically, the guidewire is advanced into and sub-selects the desired distal vasculature region of interest and then the catheter is advanced over the guidewire to a more distal position. Moreover, balloons may be attached to a delivery catheter, guidewire or guide catheter and an inflation lumen provided to allow balloon inflation and deflation to occlude at will a region of interest in a vasculature.

Also, current OCT (optical coherence tomography) imaging systems are not able to image much more than about 2 mm (typically 1.2 to 1.7 mm) into blood or tissue. Because vessels for which imaging is desired are generally 2 mm in diameter or greater and the imaging device may be in contact with a vessel wall, it is not practical to expect to image the wall of these vessels over their full 360 degree circumference to any vessel wall depth without clearing the blood from the field of view, eliminating the blood's properties impacting imaging depth and/or controlling the catheter's position relative to the vessel wall. Clearing may be accomplished by replacing the blood with a saline or other water based solution (flushing), such as by injecting the solution down the guide catheter.

The frequency of light used in OCT imaging systems is such that its wavelength is short enough for it to interact with individual red blood cells. Use of longer wavelengths to avoid the red blood cell interaction results in a loss of the desired image axial (depth) resolution for vulnerable plaque (VP) detection. The red blood cells have a slightly higher index of refraction than the plasma in which they are suspended. In addition, the red blood cells are shaped like concave lenses, so the OCT light may be re-directed and refocused (diverged) by each red cell it passes through, both to and from the tissue/vessel wall to be imaged. In addition, there are some comparatively minor light energy losses due to absorption and path length changes due to scattering (reflection) by the red cells.

IVUS (intravascular ultrasound) may also be used to image VP's at the desired resolutions, if a high enough ultrasonic frequency is used. In high frequency IVUS systems, the red blood cells are imaged and block/attenuate the ultrasound, degrading the imaging depth. Therefore, such systems will also require a flush for reasons similar to the problems of OCT.

In photodynamic therapy systems, the frequency of the light may be even higher than that used in OCT systems. Thus, to control the amount of light energy that reaches the vessel wall within acceptable limits and to limit the possible damage to the blood cells, flushing is likely to be required.

Flushing of coronary arteries to remove blood from the field of view of the OCT device, very high frequency IVUS device or path of a photodynamic therapy beam is normally accomplished by injecting saline into the vessel to be imaged, either through the guiding catheter or a catheter/sheath that surrounds/incorporates the device. However, a simple flush has quite a few drawbacks and problems:

1. When one effectively flushes, the blood is replaced/extremely diluted with another fluid, usually a saline or other isotonic biocompatible water-based solution, which has little oxygen captured in it. Thus, the time window for imaging is limited by the ischemia consequences of the solution on the heart muscle. The more proximal the flush, the more of the heart muscle is affected. Since imaging is desired in patients usually already suffering from ischemia or previous cardiac muscle ischemic tissue damage, the safe/pain-free (the patient is usually conscious during a catheter based vascular procedure) flushing time period is short.

2. Flow in coronary arteries is laminar and thus tends to flow in streamlines and not mix very rapidly with adjacent streamlines. Thus, injected solutions tend to flow in their own streamlines, leaving some areas of blood flow (some blood streamlines) not completely displaced/replaced or leaving eddies of blood at branch points or areas protected/created by the device's/catheter's/sheath's presence.

3. Most water based flushing solutions have a viscosity that is significantly less than that of blood. Thus, for the incoming flush to create enough pressure in the vessel/vessel path to exceed the blood pressure and thus relatively completely displace the incoming blood, the flow rate of the flush must exceed the normal flow rate of the blood in the vessel. In other words, the resistance to flow in the vessel is lower for the flush than for the blood. So as the flush replaces the flowing blood at the arteriole level, a greater and greater flow rate of the flush is required until a peak flow rate when the flush effectively completely replaces the blood in the artery/arterioles downstream (the flow resistance of the capillaries/arteries is negligible compared to that of the arterioles) and the arterioles are maximally opened in response to tissue ischemia. The volume of flush required can be quite high during extended flushing time periods.

4. In most injection configurations, the required high flush flow rate enters the vessel via a relatively small effective flow cross-section (catheter/sheath exit port(s)), thus the injection velocity is very high. High velocity jets can be damaging to vessel walls. Additionally, the pressures and volumes required are not easily accomplished by manual injections; an injection device is desirable. Injecting a more viscous fluid, like contrast, requires a lower flow rate, but the catheter injection pressure is relatively unchanged due to its higher viscosity. A high viscosity injectate/flush also increases the time it takes to wash out the flush (longer ischemic time after the flushing is stopped) and, of course, contrast is quite expensive relative to normal flushing solutions.

Several methods to deal with these problems have been previously suggested/disclosed:

1. To solve the problems with light, oxygenated blood could be withdrawn from the patient and materials added to the blood to increase the index of refraction of its plasma to that of the red blood cells and then use it as the flush, or this could be done systemically. This would eliminate/effectively minimize the lens effect and the reflection effects of the red blood cells. The remaining absorption effects would be minor. Since the red blood cells are oxygenated, ischemia is not a problem. It has been reported that contrast can be used to make this index of refraction change to the plasma. However, it is likely that it would be very difficult or toxic to make this adjustment systemically. It is likely somewhat easier and faster to perform this with withdrawn blood, but this would require extra equipment/disposables and a time consuming index matching procedure, as well as issues involved with increased blood exposure. The streamlines and injection problems would still be a challenge and hemolysis could be an issue.

2. The imaging can be done very rapidly by decoupling the image data gathering from the image presentation. This limits the time required for flushing and minimizes ischemia. For any given imaging time, the longer the vessel length to be imaged, the less the longitudinal resolution of the image data gathered during a controlled pullback over that length. However, calculations have shown that a significant length of vessel can be imaged in a very short time and still retain longitudinal resolutions that will allow the reliable detection of VPs. The gathered images are recorded and are accessed by the physician at a comprehensible rate/physician controlled manner. If a VP is detected and an increased longitudinal resolution is desired, another pullback of a shorter length can be performed between the pullback positions specified (positions derived from the previous pullback's presentation data). This method provides a means to reduce the ischemic time and the volume of flush solution required, but still requires high flush flow rates and doesn't deal with the problems of streamlines.

3. The distal end of a guide may be modified to deal with the problems of streamlines with guide catheter infusions or flushing. High flow rates, especially since the guide is very proximal, are still required. The guide would have to be designed to be compatible with the imaging or therapy device, and this might make it less compatible with other devices/catheters required to treat a VP or other medical condition.

4. One could image through a fluid filled balloon and eliminate the need for a flush. However, this would still have the ischemia problem, would damage the vessel wall/the VP and likely distort the vessel so its image would be distorted. Imaging a long length of vessel would be very difficult to design a balloon for, because the size of the vessel changes along its length and the balloon inflation pressure would tend to straighten the vessel (damage/distortion). A large balloon could also take a long time to deflate. Also, one would not be able to image effectively through any air trapped in the balloon, due to index of refraction differences. If the balloon were made of a fluoropolymer and/or very thin, then the balloon material wouldn't interfere significantly with the OCT light. Water/water-solution filled perfluorocarbon catheter lumens will not interfere significantly with OCT light.

5. Flushing just proximal to the length of vessel to be imaged will help limit the flush flow rate required, at least where the imaging position is distal in the vessel. This implies that the imaging be done in a catheter or a sheath, and that the imaging device engage a sheath or catheter or a flushing sheath/catheter be inserted along with the imaging device. Since the rotating OCT imaging assembly (imaging core) can be made so small, on the order of 0.004" diameter, it can be incorporated into a flushing sheath/catheter/other catheter with little size increase. Or, if the imaging device is a guidewire, use a flushing sheath to retain guidewire position after an imaging pullback. Such a system could still be as small or smaller than current IVUS catheters, which can access the vessels of interest.

Also known in the prior art are embolic protection devices, and systems for enabling the insertion and removal of embolic protection devices, for capturing and retaining embolic debris, which may be created during the performance of a therapeutic interventional procedure in a stenosed or occluded region of a blood vessel. Devices and systems of this kind include devices and systems that have a strut assembly or cage, generally self expanding, with a filter element thereover. Devices and systems of this type are disclosed in Published U.S. Patent Applications Nos. 2003/0120303, 2003/0144685, 2003/0212361, 2004/0006361 and 2004/0098032, and are sold under the trademark ACCUNET.

DETAILED DESCRIPTION OF THE PREFERRED EMBODIMENTS

Embodiments of the present invention comprise automatic occlusion/flush dispersion devices. In these devices, the occlusion/flush dispersion device deploys to occlude or partially occlude the artery (or vein) during the injection of the flushing solution. In fact, the flow or pressure of the flush injection is used to deploy (expand) the occlusion/flush dispersion device. Thus, during the flushing (or infusion), the vessel is at least partially occluded at the device site, so the flush will flow preferentially distal or proximal (depending upon the flush's exit position relative to the occlusion) into the arterial (or venous) tree and clear or dilute the path for the light or ultrasound, allowing one to more effectively introduce an agent (e.g. saline solution, angiographic contrast, ultrasonic contrast) into the region of interest or more effectively expose a therapeutic agent to a vascular region of interest, to tissues adjacent to a vascular region of interest or tissues in the direction of the flush flow. Less flush will be required because the vessel flow rate will be reduced by the occlusion/partial occlusion. Once the injection ceases, the occlusion/flushing device will collapse due to the lack of flush flow/pressure and vessel blood flow will resume as before the flush injection. Because the flush lumen and the occlusion device operating lumen can be the same lumen, the catheter can be made smaller than conventional occlusion balloons that inflate their balloon(s) via an inflation lumen and deliver the flush via a separate flush lumen. In some embodiments, the flush lumen may also be used as a guidewire lumen to further decrease the required catheter size. Smaller catheters can be positioned more distally (into smaller/more distal vessels) and require smaller introducers, resulting in lower insertion site (introducer) complications. Since the device automatically deploys during flushing and collapses at the end of flushing, there is less occlusion/flushing time required compared to balloon occlusion systems with relatively long inflation/deflation times and/or systems with separately operated flushing and occlusion lumens. Because the device can be configured to widely disperse the flush, the flush velocity is low, reducing the chance of vessel damage. Because the device disrupts blood flow and disperses the flush around the catheter, there is better mixing of the flush and blood and/or better replacement of the blood by the flush and thus, less chance of protected blood streamlines or eddies.

Figure 1:
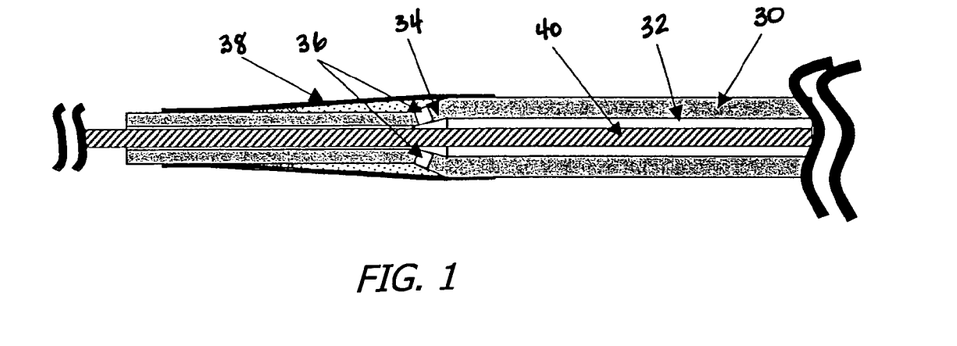
FIG. 1 is an illustration of an occlusion/flush dispersion device of one embodiment of the present invention shown in the retracted condition.
Figure 2A:
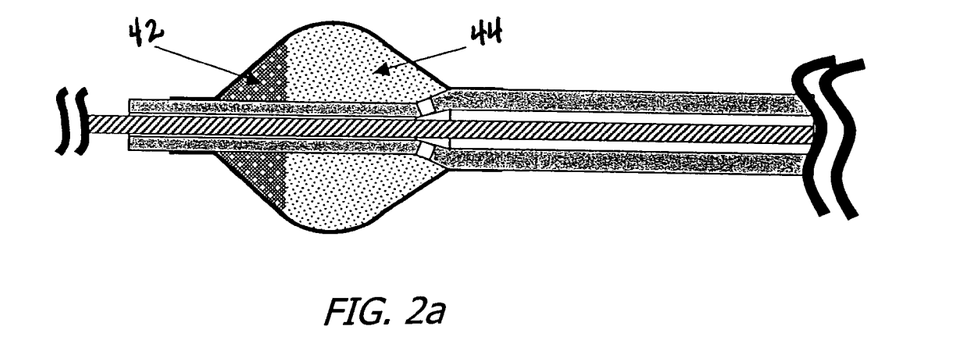
FIG. 2a is an illustration of an occlusion/flush dispersion device of FIG. 1 shown in the inflated/occlusion condition.

An example of such an embodiment may be seen in FIGS. 1 and 2a, which show the distal end of a representative automatic occlusion/flush dispersion device assembly that has been sliced through longitudinally to show its contents in cross-section. The main catheter shaft 30 has its inner diameter 32 decreased at transition section 34. Preferably, in this transition section 34, proximal to it or in its vicinity, there are holes 36 cut in the shaft wall. Normally the occlusion/flush dispersion device 38 is in the retracted condition shown in FIG. 1. However when flush is injected into the inner diameter 32 at the proximal end of the catheter shaft 30, the change in inner diameter 32 causes an increase in flush flow resistance (a flow restriction), creating a higher flush pressure to holes 36 for the same flush flow rate than if there was no inner diameter decrease. This higher pressure is used to deploy the occlusion/flush dispersion device 38 as shown in FIG. 2a when flush is flowing at a sufficiently high rate or pressure. In general, such flow restriction, however created, is configured to restrict the flow through the catheter from the holes 36 to the distal end more than the flow is restricted between the proximal end of the catheter and the holes 36, i.e., cause a greater pressure drop.

Figure 2B:
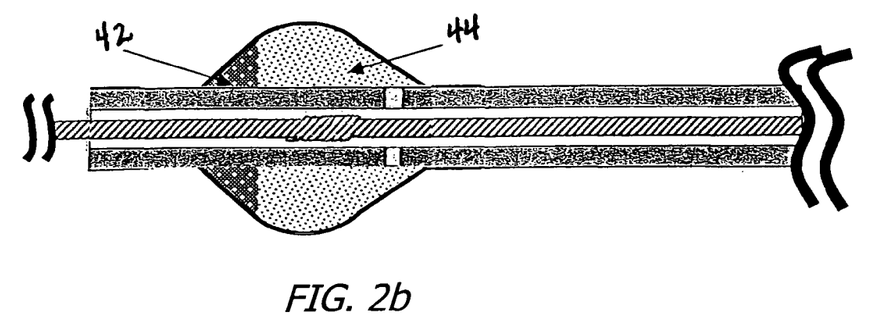
FIGS. 2b through 2f are illustrations of some alternate embodiments of the occlusion/flush dispersion device of the present invention.
Figure 2C:
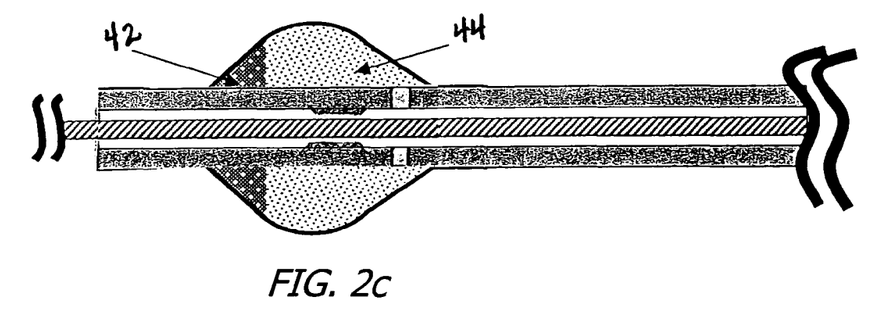
Figure 2D:
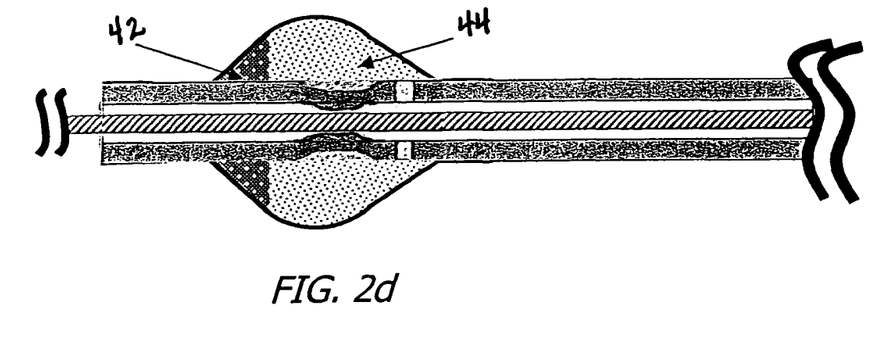
Figure 2E:
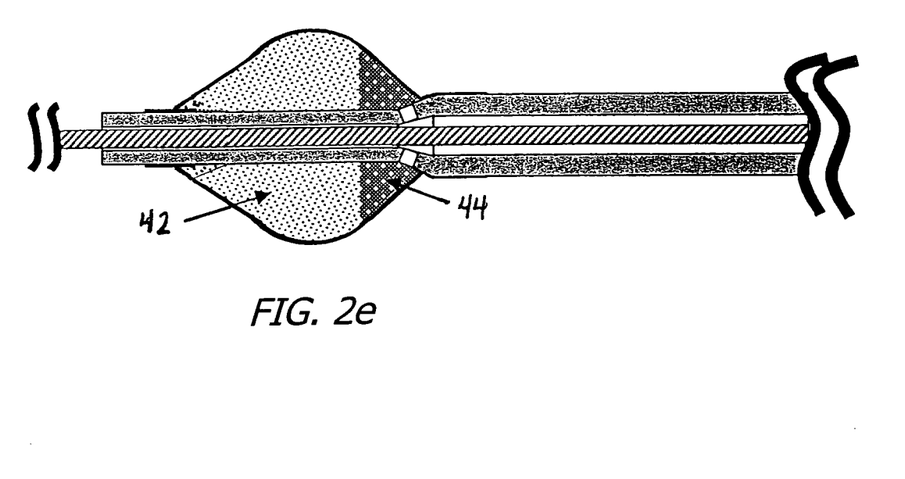
Figure 2F:
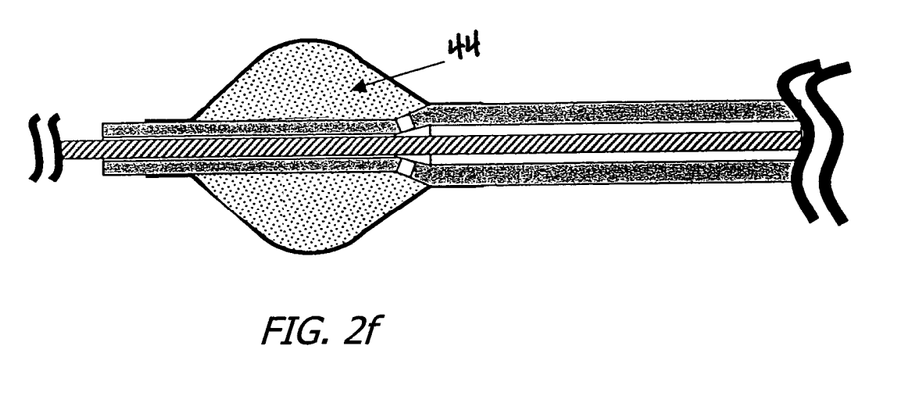

Also shown is a center member 40, which is used in some embodiments to further increase the flush pressure. This center member may be a guidewire, used also for normal distal access and vessel sub-selection functions. In other embodiments, the center member 40 may not be a guidewire, but may be the optical fiber 40 or IVUS core 40. In other embodiments, the center member 40 may be a moveable and/or removable member 40 that may include a lumen(s) or other catheter-like features. In other embodiments, the center member 40 may include an OD increase distal to holes 36 to provide a flow resistance increase due to the restriction of the flow space between the center member 40 and the inner diameter 32. In other embodiments, an OD increase on the center member may replace the functions of the transition section 34 and thus, the change in the inner diameter 32 may be omitted. This is shown in the embodiment of FIG. 2b. In still other embodiments, a local restriction may be placed inside the catheter 30, as shown in FIG. 2c, or the catheter shaft itself may be necked down locally to form the restriction, as shown in FIG. 2d. The occlusion/flush dispersion device 38 is, in effect, expanded or deployed by the flowing flush as it is forced out of the holes 36 and into the occlusion device 38. In one embodiment, a material similar to that used in the embolic filters hereinbefore referred to covers the device 38, except that it covers the entire device 38 and only has holes in its distal portion 42. The proximal portion 44 is without holes and thus forms a barrier to proximal flush flow or blood flow in the artery (or vein). The injected flush that flows through holes 36 inflates the occlusion/flush dispersion device 38 and flows distally out of the holes in the distal portion 42, the holes in the distal portion 42 providing a restriction for a suitable flow rate with an associated increase in pressure in the occlusion/flush dispersion device 38 for inflation. In some embodiments, there is another flush distal flow path(s) out of the occlusion/flush dispersion device, such as if the distal end of the device 38 where mounted on a sliding ring or tube section, as shall be described with respect to the embodiment of FIG. 5. In some embodiments, there is a significant flow path out of the distal end of the inner diameter 32. In another embodiment, the proximal portion 44 is provided with holes and the distal portion 42 is without holes, such that the distal portion 42 forms a barrier to distal flush flow or blood flow in the artery (or vein). Such an embodiment is shown in FIG. 2e. In another embodiment, there are no holes in the distal portion 42 and the proximal portion 44, such that the device operates as purely an occlusive device and relies solely on flow paths other than these holes for the device to collapse after the flush. Such an embodiment is shown on FIG. 2f.

When the flush injection is completed (no or low flush flow), the occlusion device 38 collapses as shown in FIG. 1. It collapses because the material (42,44) that covers the occlusion device 38 is attached to an elastic skeleton whose undeformed shape is to hug or be very close to the outer diameter of the catheter shaft 30 inside of occlusion device 38. The attachment points or areas of the cover material (42, 44) to the skeleton may be fixed attachments and/or sliding attachments. As the occlusion device 38 collapses, the flush solution in it is forced out the holes in its distal portion 42, forced back into the inner diameter 32 via holes 36 and/or forced out via other previously mentioned flush flow paths. In some embodiments, the collapse of the occlusion device 38 may be assisted by the withdrawal of the device on which it is mounted proximally into the inner diameter of a sheath, catheter or guide catheter (or via the same relative motion between the components) or by applying a negative pressure (below atmospheric) to the inner diameter 32 at the proximal end of the catheter shaft 30 for a short time.

Figure 3:
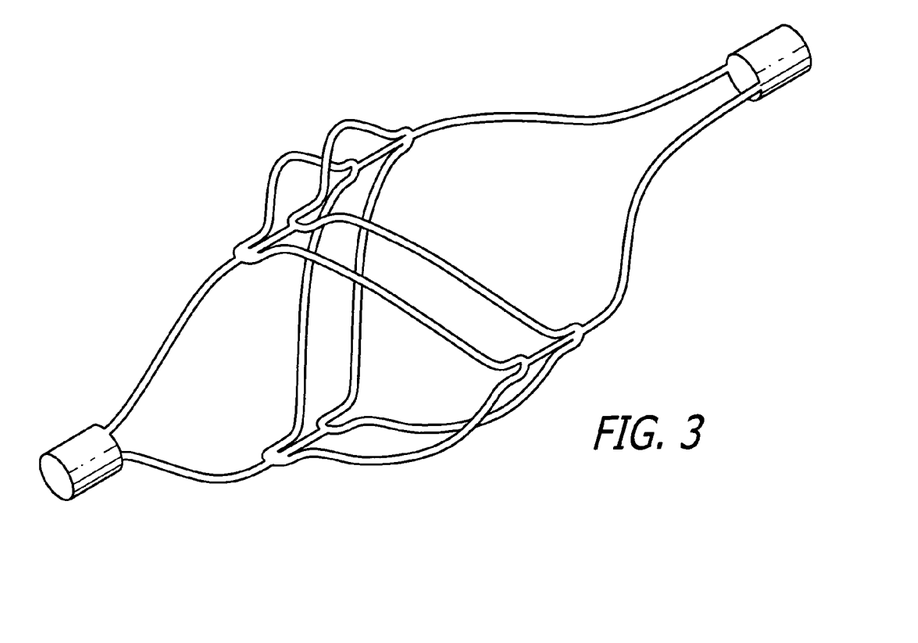
FIG. 3 illustrates one example of an elastic skeleton usable with embodiments of the present invention, shown in the expanded state.
Figure 4:
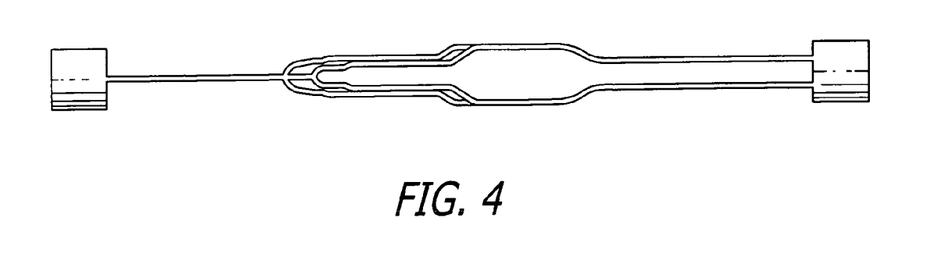
FIG. 4 illustrates the elastic skeleton of FIG. 3 shown in the unexpanded state.
Figure 5:
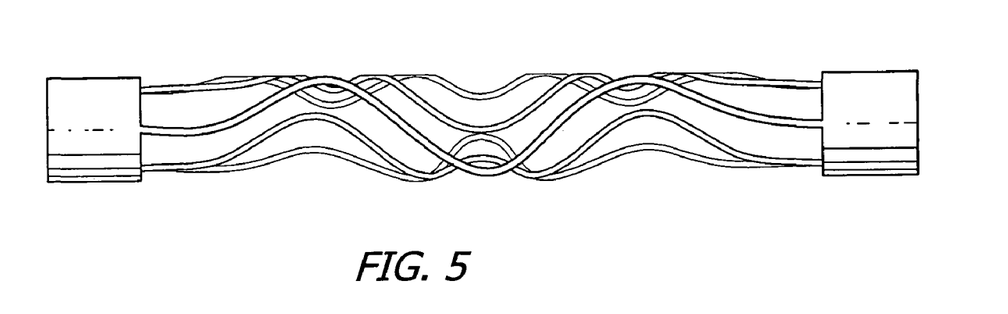
FIG. 5 illustrates another elastic skeleton shown in the unexpanded state.

The elastic skeleton can take on many shapes and be made of many different materials with suitable elastic properties, such as NiTi and elastomeric polymers. A simple example would be a shade like used in the embolic protection devices hereinbefore referred to as shown in FIG. 3, but left in its un-expanded condition or set to an inner diameter similar to the outside diameter of the catheter shaft 30 inside the device 38, as shown in FIG. 4. By way of example, a NiTi tube of the proper diameter(s) may be cut in the desired skeleton pattern, cleaned, held in a fixture and exposed to heat to set the NiTi to the desired undeflected diameter and/or shape. Another skeleton example would be to use two or more zigzag (curved points) or sine wave-like shapes that run longitudinally across and/or laterally around the material as shown in FIG. 5. Another skeleton example would be to use one or more zigzag (curved points) or sine wave-like shapes (either connected to each other or not connected) that run laterally around the material and the shaft (this configuration in the connected condition is the shape of conventional stents). Yet another skeleton example would be a shape having a sliding ring or tube section at either end, such as ring 52 or ring 48 in FIG. 6. In some embodiments, the design of the skeleton and the attachment method/material of the cover material may be chosen such that both ends of the device may be stationary relative to the shaft during device expansion, such as the embodiment shown in FIG. 5. In some embodiments, a ring (s) may be omitted and the cover material (42,44) directly attached to the shaft. In some embodiments, the skeleton is not connected to the shaft at its distal end and/or its proximal end. In some skeleton embodiments, finger-like skeleton projections may also be included that are also attached to the cover material (42,44) to aid in the predictability of the material's (42,44) collapse sequence and its resulting collapsed profile. For instance, if a finger applies a greater collapsing force to the material (42,44) than the adjacent portions of the skeleton, then that potion of the material (42,44) will collapse more rapidly toward the shaft 30 than the adjacent portions. In conjunction with preset folds in the cover material (42,44), the use of such fingers can result in a substantially reduced and predictable collapsed profile of the device. In some skeleton designs that include the rings and/or ring and link structures/shapes of conventional stent designs, this controlled collapse function may also be facilitated by the differences in the designed collapsing forces of adjacent rings.

One advantage of this invention is that the flush flow velocity to which the vasculature is exposed can be made much lower, because the effective flow cross-sectional area of the distal portion 42 can be made larger than that of the inner diameter of the catheter shaft 30 or the effective area of any port that may be cut into a flush lumen. Additionally, the volumetric flowrate out of any hole in distal portion 42 can be much smaller than the flowrate out of the inner diameter of the catheter shaft 30 or the effective area of any port that may be cut into a flush lumen. Thus, that lower flowrate flush mixes with the adjacent much lower velocity blood or other flush and slows down in a much shorter distance than the flow out of the inner diameter of the catheter shaft 30 or any port that may be cut into a flush lumen. A lower flow velocity reduces the chances that the flush flow stream will cause injury to the vessel wall. The flush slowing down in a shorter distance reduces the chances that a flush flow stream with an injurious high flow velocity will reach the vessel wall.

Figure 6:
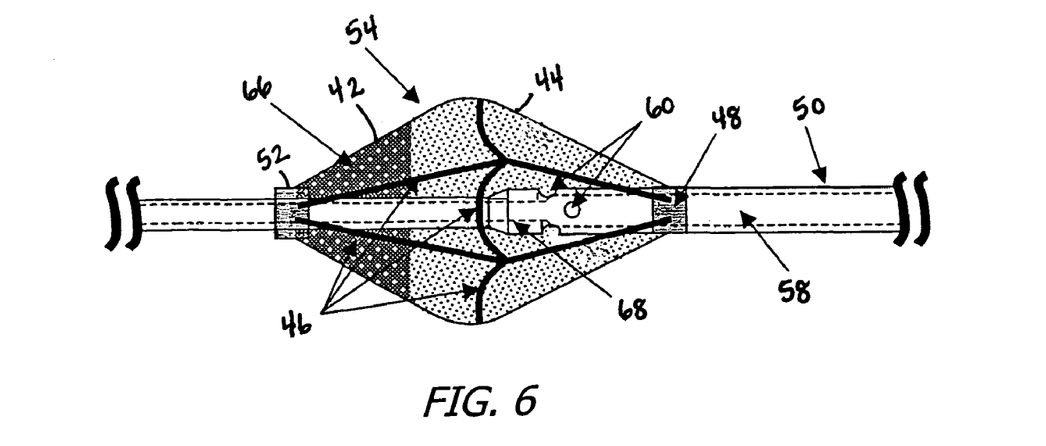
FIG. 6 illustrates another embodiment having a sliding ring or tube section at either end of the elastic skeleton.
Figure 7:
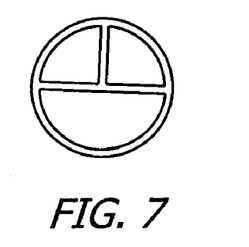
FIG. 7 illustrates a cross section of a multiple lumen cannula useable with the present invention.

Now referring specifically to FIG. 6, the material 42,44 of FIGS. 2 and 6 has been cut away on the near side to expose parts of the NiTi skeleton 46. In this case, the skeleton 46 is similar to skeletons used in the embolic protection devices hereinbefore referred to, except that the rest or undeflected condition of the skeleton 46 is a collapsed state where the skeleton 46 hugs the catheter shaft 50 or is much closer to the catheter shaft 50. On its proximal end, the skeleton 46 is attached to a mounting ring 48. The mounting ring 48 is attached to the catheter shaft 50. The distal end of the skeleton 46 is attached to the sliding ring 52. When the flush flow is low or stopped, the sliding ring 52 moves distally as the occlusion device 54 collapses due to the elastic forces of the skeleton. In this embodiment, the flush may flow out of the gap between the inner diameter of the sliding ring 52 and the outer diameter of the catheter shaft 50, as well as out of the holes 66 in the distal cover material 42 and holes 60 into the inner diameter 58. In another embodiment, holes 66 may be omitted and during flushing and collapse of the occlusion device 54 the bulk of the flush flow may exit inner diameter 58 distal of the occlusion device 54. While only one inner diameter 58 is shown in this Figure, it should be noted that several lumens may be incorporated in catheter shaft 50, some of which may be in communication and accept at least a small portion of the flush flow. For instance the guidewire lumen and the imaging device (or optical fiber) lumen in a multiple lumen cannula such as shown in FIG. 7 may also include flush flow and holes 60 (FIG. 6). This type of arrangement has the advantage of helping to flush air bubbles out of the catheter lumens. Air may interfere with light or acoustic transmission.

This concept can be further expanded to include embodiments where imaging or light transmission occurs inside the occlusion/flush dispersion device. This has an additional advantage over a balloon; air may be trapped in a balloon, but this is very much less likely inside an occlusion/flush dispersion device. In such devices for use with light, the material covering (42,44) may be a fluorocarbon material, perhaps an expanded fluorocarbon material, to more closely match the index of refraction of blood/flushing solution and aid in light transmission (limit reflection).

It is a straightforward engineering exercise to design the device and catheter system to obtain the desired deployment (partial occlusion) or occlusion pressure (full occlusion) at the desired flush flow rate or flow rate range. The flow rate can be controlled to make such a system safer using a controlled pump. If the pump is connected/controlled by the imaging system or photodynamic system controller, the deployment of the occlusion/flush dispersion device can be timed to further reduce flushing time. If imaging (or light application) is done inside the occlusion/flush dispersion device, the flow rate may be adjusted by the imaging system (or photodynamic system) controller to control the occlusion/flush dispersion device's deployment or occlusion pressure based on image information (i.e. occlusion/flush dispersion device outside diameter, vessel outside diameter) or other detected information (i.e. reflected light levels).

Figure 8A:
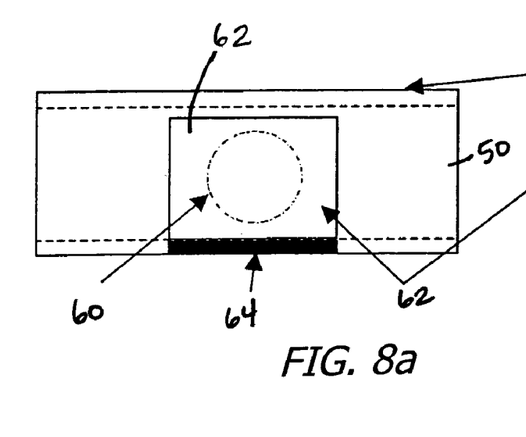
FIGS. 8a and 8b illustrate a flap allowing rapid deployment/inflation and slower deflation of an occlusion device in accordance with an embodiment of the present invention.
Figure 8B:
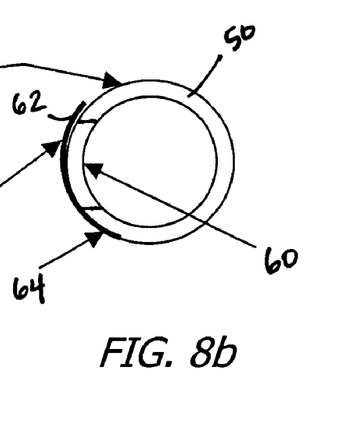
Figure 9A:
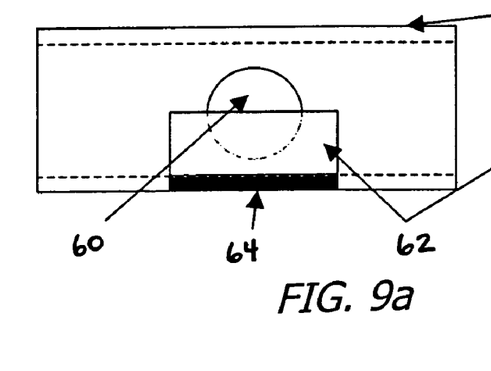
FIGS. 9a and 9b illustrate the flap of FIGS. 8a and 8b as unobstructing flow during inflation of an occlusion device.
Figure 9B:
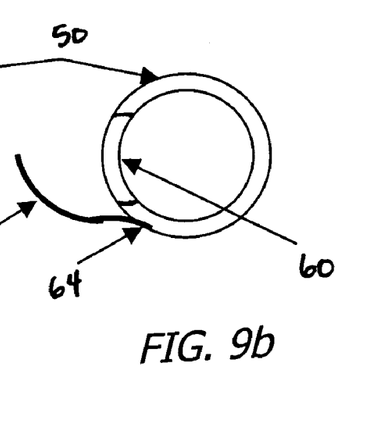

The occlusion devices of FIGS. 1, 2 and 6 may also be deployed to occlude or partially occlude a vein (e.g. Coronary Sinus, Great Cardiac vein) during the injection of a contrast solution. In fact, the flow or pressure of the contrast injection will be used to deploy the occlusion device. Thus, during contrast injection the vessel is at least partially occluded proximal of the injection site, so the contrast will flow preferentially distal into the venous tree and provide better visualization. As before, once the injection ceases, the occlusion device will collapse due to the lack of contrast flow/pressure and vessel blood flow will resume as before the contrast injection. When used for injection of a contrast solution into the coronary veins or coronary sinus (CS), the automatic occlusion (or partial occlusion) device is preferably mounted somewhat proximal on the inner guide (but still in the CS) or distally on the outer guide of a conventional CS access system. Also preferably, most of the contrast flow would be out of the distal end of the inner guide to provide a better view of the distal coronary venous anatomy. If the device is mounted on the outer guide, contrast injected into the outer guide ID (to deploy the device) may flow into the inner guide via holes cut in the wall of the inner guide, proximally. The device would be typically used as a partial occlusion device, and if of the design of FIGS. 1, 2 and 6, the occlusion device would collapse rapidly after the contrast injection was completed. What is preferred is for the device to deploy (expand to size) rapidly and then to collapse (return to a small outer diameter near the outer diameter of the guide) much more slowly. Thus, the preferred device would inhibit CS outflow for a longer period of time and thus, provide for a longer time that the coronary venous anatomy could be observed by fluoroscopy. While the collapse time could be controlled by device design, there are limits as to how much different the deployment and collapse times can be controllably made. What is needed is a simple way to provide a rapid deployment that requires little contrast flow out of the device and at the same time provides a more easily controlled and longer device collapse/retraction time. This may be achieved by providing a small flap(s) 62 (FIGS. 8a and 8b) on the catheter shaft 50 outer diameter that covers the shaft hole(s) such as holes 60 in FIG. 6 that feed contrast into the device to deploy (expand) it. Thus, during contrast injection (and whenever the pressure in the catheter shaft inner diameter exceeds the pressure inside the device by a small amount), the flap(s) 62 would be pushed away from the hole(s) (FIGS. 9a and 9b), allowing rapid contrast flow into the device to rapidly deploy the occlusion device and keep it deployed. Once contrast injection is stopped, the small flap(s) 62 will cover the hole(s) 60 (FIGS. 8a and 8b) and not allow an appreciable amount of contrast flow back into the shaft inside diameter from inside the device. The collapse time of the device is substantially controlled by the collapsing forces of the skeleton 46 (the greater the pressure/elastic force of the skeleton 46 applied to the material (42, 44), the faster the collapse) and the flow resistance of the contrast out of the device (the greater the flow resistance, the longer the collapse time). The flap(s) 62 considerably increases the flow resistance of the contrast out of the inflated device, so the collapse time of the device will be considerably increased. Since the flap(s) 62 are pushed away from the holes 60 in the outer diameter of the shaft 50 during device deployment, there is little effect on its deployment time. The collapse time may be adjusted by adjusting the skeleton 46 collapsing forces (pressure), the size and number of the holes 66 in the cover (flow resistance, less holes=greater flow resistance, smaller holes=greater flow resistance), if any, and the flow resistance of the gap between the sliding ring 52 (FIG. 6) and the shaft outer diameter (if a sliding ring 52 is used). The greatest flow resistance and longest collapse time will be when there are no holes in the cover (42, 44). With little, less or no flow of contrast out of the cover (42, 44) or out of the gap (if used) during a contrast injection, the bulk of the contrast will flow down the inner diameter of the inner guide and out its distal end during contrast injection, as desired.

Figures 10A, 10B:
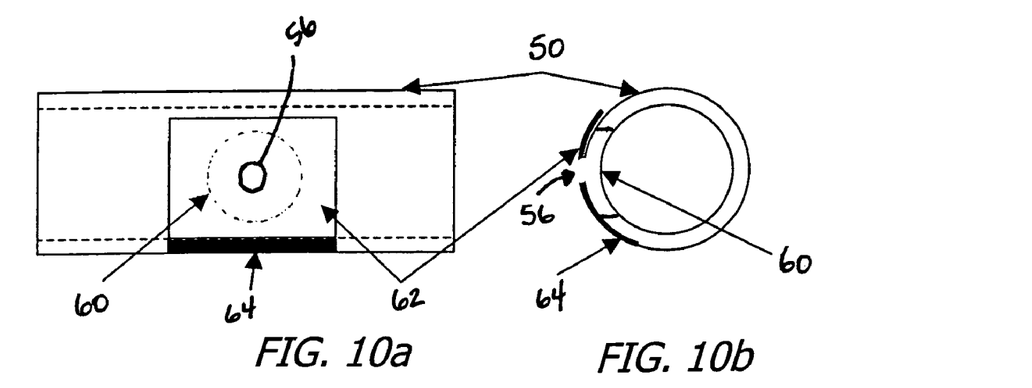
FIGS. 10a and 10b illustrate a flap implementation similar to that of FIGS. 8a and 8b, though having a small hole therein to restrict rather than prevent flow back into the catheter.
Figures 11A, 11B:
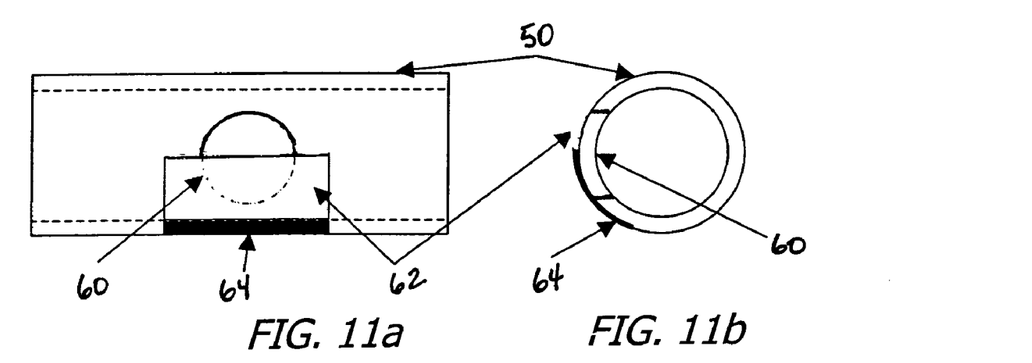
FIGS. 11a and 11b illustrate a flap implementation similar to that of FIGS. 8a and 8b, though with the flap only partially covering a hole in the catheter to restrict rather than prevent flow back into the catheter.
Figures 12A, 12B:
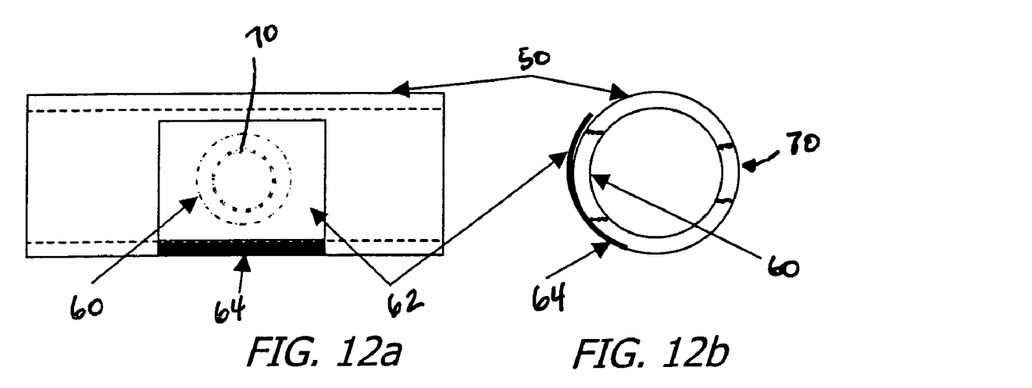
FIGS. 12a and 12b illustrate a flap implementation similar to that of FIGS. 8a and 8b, though with an additional hole in the catheter to restrict rather than prevent flow back into the catheter.

In some designs, it may be advantageous to place a small hole(s) 56 in the flap(s) as in FIGS. 10a and 10b (or have the flap(s) incompletely cover the hole(s) in the outer diameter of the shaft as in FIGS. 11a and 11b as a failsafe or as another contrast flow path (another method to lower or control the flow resistance of contrast flow out of the device). Thus, if the other flow path(s) out of the inside of the device 54 becomes blocked with debris or thrombus, the device 54 will still be able to collapse or be able to be collapsed by the inner diameter of the outer guide when it is pulled back inside the outer guide. Additionally or alternatively, if there are several holes in the shaft, one or more holes 60 may not be provided with a flap to act as a failsafe, as illustrated by the inclusion of uncovered hole 70 in FIGS. 12a and 12b.

Because the flap(s) 62 will be inside the device 54, it (they) will be protected by the device 54 from contact with the vessel, outer guide inner diameter and other anatomy or devices. When blocking flow they will also be curved about one axis, resisting deflection about another axis. Thus, the flaps can be made of very thin materials (i.e. thermoplastics, elastomers, etc.), as they need not be very robust to maintain their structural integrity. Therefore, the addition of the flaps 62 need not appreciably increase the outer diameter of the inner guide, outer guide or device.

A simple construction method would be to cut the flap(s) out of a thin section of guide jacket material tubing and fuse a portion 64 of the flap(s) near the hole(s) 60 on the shaft outer diameter to the guide jacket or shaft 50 to attach it in place. Laser bonding the flap(s) 62 to the jacket to create the fused portion(s) is an ideal method. Alternatively, hot air fusing may be used. A thin piece of a non-miscible/higher melt temperature material, like a PTFE or FEP tube section, can be used to hold the flap 62 in place and provide the fusing force. A heat shield and/or heat sink over the portion of flap(s) 62 that must be free to move can be used to prevent it from fusing with the guide's jacket or distorting. Naturally, any attachment means may be employed to attach or hold the flap(s) 62 in position over the hole(s) 60 in the outer diameter of the shaft.

Referring again to FIG. 6, the material (42,44) has been cut away on the near side to expose parts of the NiTi skeleton 46. The distal material 42 may be provided with holes 66 to allow flush flow (the flush may be contrast (an image enhancing agent), a contrast solution, a therapeutic solution, an energy transmission enhancing solution and/or any other fluid solution) out of the device 54 to aid in its collapse (return to its undeployed condition) or provide diffusion of the flush distal of the device 54. In embodiments where flow out of the device 54 is desired to be minimized, few holes 66 may be located in either the distal 42 or proximal 44 material, or holes 66 may be omitted from the material (42,44) entirely. Holes 60 provide for flush flow into and out of the device 54 via the inner diameter 58 of shaft 50. The inner diameter 58 of shaft 50 may have a reduced inner diameter portion 68 that increases the flush flow resistance and thus increases contrast pressure during flush flow to provide the pressure required to rapidly deploy device 54. In another embodiment, the inner diameter and outer diameter of the shaft 50 may be reduced in the area of device 54 to provide the increased contrast pressure and/or to keep the OD of device 54 in its undeployed state close to or smaller than the outer diameter of the shaft 50. In this embodiment, the rest condition (undeployed state) of the skeleton 46 is a collapsed state where the skeleton 46 hugs the shaft 50 or is very close to the shaft 50. When the flush flow is high enough, the sliding ring 52 moves proximally as the occlusion device 54 deploys (expands). When the flush flow is low or stopped, the sliding ring 52 moves distally as the occlusion device 54 collapses. In this embodiment, the flush may flow out of the device 54 during its collapse via the gap between the inner diameter of the sliding ring 52 and the outer diameter of the shaft 50, as well as out of the holes 66 in the distal (and/or proximal) cover material 42,44 and the holes 60 via the inner diameter 58 of shaft 50.

The various embodiments of the present invention disclosed herein use an expandable skeleton, which skeleton may be made in many ways. One particular method of making the skeleton already mentioned herein is to cut a thin-walled tubular member, such as nickel-titanium hypotube, to remove portions of the tubing in the desired pattern for each strut or finger, leaving relatively untouched the portions of the tubing which are to form each strut. The tubing may be cut into the desired pattern by means of a machine-controlled laser. In the case of devices disclosed herein that have a collapsed free state, as in the embodiments such as that of FIGS. 1, 2 and 6, the patterned tubing could be held in the as cut condition/pattern when heated to set its shape, or even deformed radially inward a bit to provide a preload toward the collapsed condition when in use to effectuate the complete collapse desired.

The tubing used to make the skeleton could be made of other suitable biocompatible metallic materials such as spring steel. Elgiloy is another material that could possibly be used to manufacture the skeleton. Also, polymers could be cut or formed using conventional polymer possessing, cutting and/or forming techniques to manufacture the skeleton, provided they are sufficiently flexible and bendable.

Figure 13:
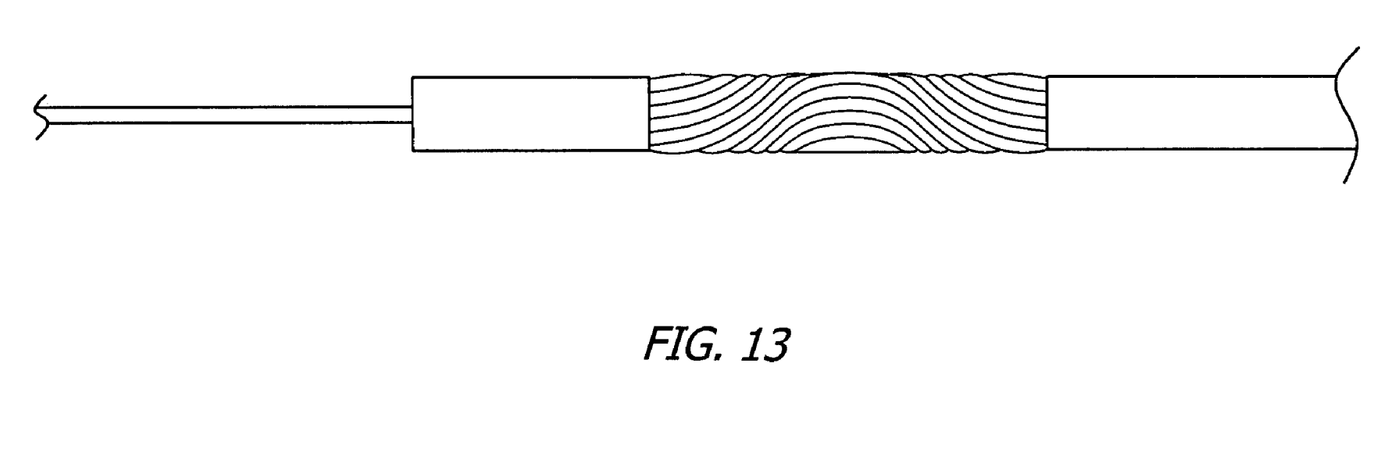
FIG. 13 illustrates an embodiment of the occlusion/flush dispersion device of the present invention having preset folds in the covering of the device.

The polymeric material which can be utilized to create the covering for the devices of the disclosed embodiments of the present invention include, but are not limited to, polyurethane, polyester and Gortex, a commercially available expanded fluorocarbon material. Other possible suitable materials include ePTFE. The material can be elastic or non-elastic, woven or non-woven. In that regard, elastic as used herein means stretchable, whereas non-elastic means relatively non-stretchable, though in either event, the material must be readily foldable without cracking or other failure, and in some embodiments, have a memory so as to have a bias tending to cause the material to return to the folded state unless forcibly held in an inflated state. The wall thickness of the covering can be about 0.00050-0.0050 inches. The wall thickness may vary depending on the particular material selected. The material can be made into a cone or similarly sized shape utilizing for example, blow-mold technology or dip technology. The holes can be any different shape or size. A laser, a heated rod or other process can be utilized to create the holes in the covering material or the holes may be a consequence of the weave or expansion of the material. The holes would, of course, be properly sized and numbered to provide the desired flow rates and restrictions. The holes could be lazed in a spiral pattern or some similar pattern that will aid in the re-wrapping or folding of the media during closure of the device. The end result is a porous covering portion, whether created by holes in that portion of the cover, by the weave forming that portion of the cover or by some other characteristics of that portion of the cover or its preparation. Additionally, the material can have a "set" put in it much like the "set" used in dilatation balloons to make the material rewrap or fold more easily and predictably when transitioning to the collapsed condition. Such an embodiment is shown in FIG. 13. As shown therein, in this embodiment, the flexible cover wraps around the catheter shaft as it collapses. In such an embodiment, the skeleton may be cut and set with ribs similarly shaped and hugging the catheter shaft, so that the skeleton can expand in a manner similar to the cover, and help encourage folding as set during deflation.

Figure 14A:
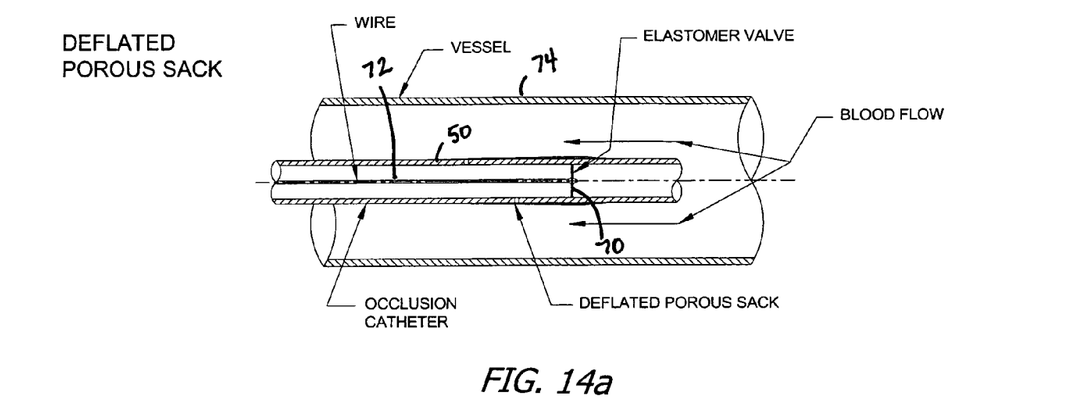
FIGS. 14a through 14c illustrate an embodiment of the occlusion/flush dispersion device of the present invention having an elastomeric valve within the catheter of the device.
Figure 14B:
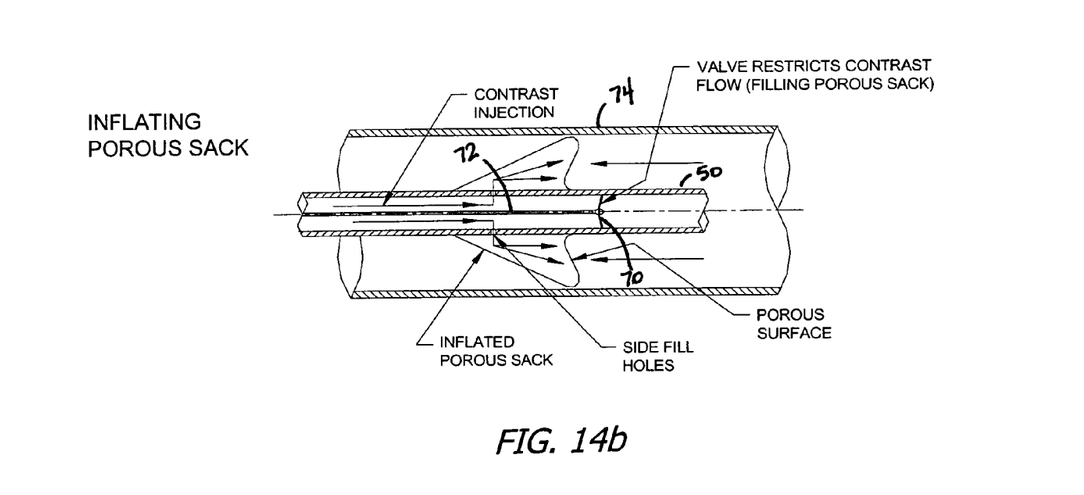
Figure 14C:
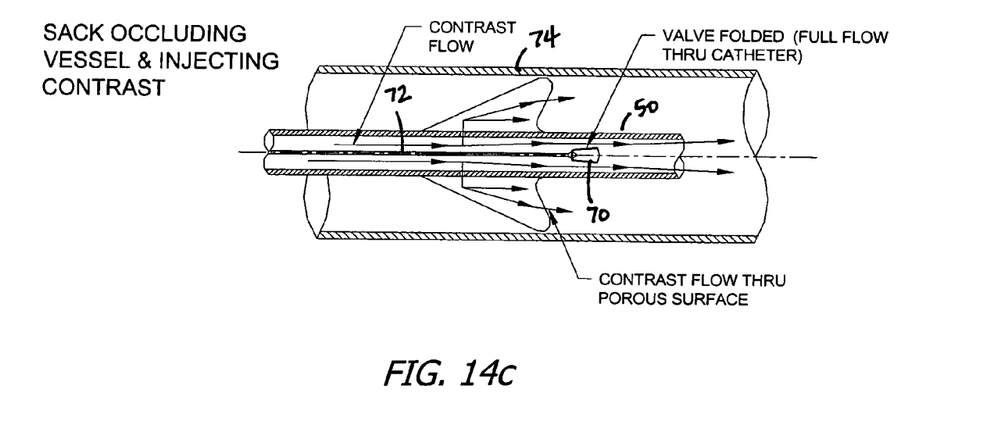

Now referring to FIGS. 14a through 14c, a further alternate embodiment may be seen. In this embodiment, instead of using a step-down in the inner diameter of the catheter to concentrate the pressure drop in the catheter at the openings to the inflatable occlusion/flush dispersion device 38, an elastomeric valve may be used, such as in an otherwise constant inner diameter catheter. Thus as shown in FIG. 14a, an elastomeric valve 70 is shown blocking or at least substantially blocking the distal end of the catheter 50 within vessel 74. The valve is supported by a wire 72, in turn supported either from the proximal end of the catheter or from a substantially non-obstructing support within the catheter. Such a valve will deflect slightly, like a diaphragm, when subjected to low pressures, as shown in FIG. 14b, allowing the flow to go exclusively or primarily to inflate the occlusion/flush dispersion device 38 shown schematically, but when the occlusion/flush dispersion device 38 is inflated to occlude the artery (or vein), an increase in pressure such as resulting from no further inflation of the occlusion/flush dispersion device 38 will cause the valve 70 to collapse, as shown schematically in FIG. 14c. In that regard, the initial diaphragm-like deflection of the elastomeric valve causes circular compression stresses in the elastomeric material, though the valve will remain as a surface or volume of revolution. At some larger pressure, the circular compression stresses will cause the valve shape to become unstable, forming pleats in the elastomeric valve like in a coffee filter, allowing it to collapse further with little increase in pressure. Thus such an elastomeric valve can serve a safety function, assuring the occlusion/flush dispersion device 38 will properly inflate at some minimum flow rate or pressure, but will prevent over pressuring the occlusion/flush dispersion device 38 if the flow rate or pressure is too high, even momentarily. The elastomeric valve can thus act as a pressure regulator, reducing the flow rate/pressure control requirements during use of the system.

Thus while certain preferred embodiments of the present invention catheter mounted automatic vessel occlusion and flush dispersion devices have been disclosed and described herein for purposes of illustration and not for purposes of limitation, it will be understood by those skilled in the art that various changes in form and detail may be made therein without departing from the spirit and scope of the invention.

What is claimed is:

1. A catheter mounted automatic vessel occlusion and flush dispersion device comprising:
  a catheter shaft having an inner diameter and an outer diameter and open proximal and distal ends;
  an expandable skeleton over the catheter shaft adjacent the distal end, the expandable skeleton having first and second ends and being non-inflatable, but elastically deflectable radially outward between the first and second ends and not elastically deflectable radially outward at the first and second ends of the expandable skeleton;
  a flexible covering over the expandable skeleton extending from the first end to the second end of the expandable skeleton to occlude a blood vessel when inflated by flushing fluid flow in the catheter shaft, the flexible covering being attached to the expandable skeleton to expand the expandable skeleton when the flexible covering is inflated, the attachment of the flexible covering to the expandable skeleton causing the flexible covering to collapse with the expandable skeleton when flushing fluid flow in the catheter shaft stops; and, at least one opening between the inner diameter of the catheter shaft and the flexible covering to cause inflation of the flexible covering when the flushing fluid flow is provided in the catheter shaft;

the flexible covering being attached to the expandable skeleton so that the expandable skeleton conforms to the shape of the flexible covering when the flexible covering is inflated;

the expandable skeleton being a biocompatible metallic member set in a collapsed state so that the expandable skeleton hugs the catheter shaft outer diameter when there is no flushing fluid flow in the catheter shaft, automatically forcing the flexible covering attached thereto to a deflated state both before flushing fluid flow in the catheter shaft begins and after flushing fluid flow in the catheter shaft stops;

a first end of the flexible covering being porous to allow flushing fluid flow when inflated to occlude or partially occlude an artery or vein at a single location during injection of the flushing fluid, a second end of the flexible covering opposite the first end not being porous.

2. The device of claim 1 wherein a proximal end of the flexible covering is not porous, and a distal end of the flexible covering is porous for controlled flow of flushing fluid out of the porous portion when the flexible covering is inflated by flushing fluid flow in the catheter shaft.

3. The device of claim 1 wherein a distal end of the flexible covering is not porous, a proximal end of the flexible covering is porous for controlled flow of flushing fluid out of the porous portion when the flexible covering is inflated by flushing fluid flow in the catheter shaft.

4. The device of claim 1 further comprising a flow restriction restricting but not blocking flow through the catheter shaft from the at least one opening and the distal end of the catheter shaft more than the flow is restricted between the proximal end of the catheter shaft and the at least one opening.

5. The device of claim 4 wherein the inner diameter of the catheter shaft is reduced in a region between the at least one opening and the distal end of the catheter shaft.

6. The device of claim 4 further comprising an elongate object within the catheter shaft, the elongate object creating the flow restriction by having an increased outer diameter between the at least one opening and the distal end of the catheter shaft.

7. The device of claim 6 wherein the elongate object is a guide wire extending through the catheter shaft.

8. The device of claim 4 further comprising a optical fiber extending through the catheter shaft.

9. The device of claim 4 further comprising an intravascular ultrasound core extending through the catheter shaft.

10. The device of claim 1 wherein the at least one opening between the inner diameter of the catheter shaft and the flexible covering is at least partially covered with a flexible flap attached to the catheter shaft to unobstruct flow of flushing fluid through the at least one opening from the catheter shaft to inflate the flexible covering and to at least partially obstruct flow of flushing fluid back into the catheter shaft when the flexible covering is deflated.

11. The device of claim 10 wherein the flap has a hole therein smaller than the opening between the inner diameter of the catheter shaft and the flexible covering.

12. The device of claim 10 wherein the at least one opening between the inner diameter of the catheter shaft and the flexible covering is a plurality of openings, less than all the openings being at least partially covered with flaps.

13. The device of claim 1 wherein the flexible covering is an elastic flexible covering.

14. The device of claim 1 wherein the flexible covering is an inelastic flexible covering.

15. The device of claim 1 wherein the catheter shaft is a multiple lumen catheter shaft.

16. The device of claim 1 further comprised of an elastomeric valve in the catheter shaft between the at least one opening and the distal end of the catheter shaft, the elastomeric valve obstructing flow through the distal end of the catheter shaft at low flushing fluid pressures on the elastomeric valve, and deflecting at higher flushing fluid pressures to present reduced flow obstruction.

17. The device of claim 16 wherein the elastomeric valve comprises a circular elastomeric member supported concentrically with respect to the catheter shaft inner diameter by a support coupled to the circular elastomeric member at its center.

18. The device of claim 1 wherein the first and second ends of the flexible covering are each fixed with respect to the catheter shaft.

19. The device of claim 1 wherein the first end of the flexible covering is fixed with respect to the catheter shaft and the second end of the flexible covering is coupled to a ring adapted to slide with respect to the catheter shaft in response to inflation of the flexible covering.

20. The device of claim 1 wherein the biocompatible metallic member is a nickel titanium member.

* * * * *